United States Patent [19]
Rise

[11] Patent Number: 5,824,021
[45] Date of Patent: Oct. 20, 1998

[54] METHOD AND APPARATUS FOR PROVIDING FEEDBACK TO SPINAL CORD STIMULATION FOR ANGINA

[75] Inventor: Mark T. Rise, Monticello, Minn.

[73] Assignee: Medtronic Inc., Minneapolis, Minn.

[21] Appl. No.: 898,102

[22] Filed: Jul. 22, 1997

Related U.S. Application Data

[63] Continuation of Ser. No. 637,259, Apr. 25, 1996, abandoned.

[51] Int. Cl.$^6$ ................................................ A61N 1/08
[52] U.S. Cl. ............................................................. 607/46
[58] Field of Search ............................. 607/4, 9, 18, 44, 607/46, 117

[56] References Cited

U.S. PATENT DOCUMENTS

| | | | |
|---|---|---|---|
| 5,058,584 | 10/1991 | Bourgeois | 607/46 |
| 5,067,960 | 11/1991 | Grandjean | |
| 5,199,428 | 4/1993 | Obel et al. | 607/44 |

OTHER PUBLICATIONS

Eliasson et al., "Spinal Cord Stimulation In Angina Pectoris With Normal Coronary Arteriograms", *Coronary Artery Disease*, vol. 4, No. 9, pp. 819–827 (1993).

Mannheimer et al., "Effects of Spinal Cord Stimulation in Angina Pectoris Induced by Pacing and Possible Mechanisms of Action", *BMJ*, vol. 307, No. 21, pp. 477–480 (Aug. 1993).

Hammermeister et al., "Cardiac and Aortic Pain", *Pain in the Chest*, pp. 1001–1042 (Date unknown).

Van Horne et al., "Multichannel Semiconductor–Based Electrodes for In Vivo Electrochemical and Electrophysiological Studies in Rat CNS", *Neuroscience Letters*, vol. 120, pp. 249–252 (1990).

Murphy et al., "Dorsal Colmn Stimulation for Pain Relief from Intractable Angina Pectoris", *Pain*, vol. 28, pp. 365–368 (1987).

Hammermeister et al., "Variables Predictive of Survival in Patients with Coronary Disease. Selection by Unvariate and Multivariate Analyses from the Clinical, Electrocardiographic, Exercise, Arteriographic and Quantitative Angiographic Evaluation", *Circulation*, 59:421–429 (1979).

Cohn, P.F., "Total Ischemic Burden: Pathophysiology and Prognosis", *American Journal of Cardiology*, No. 59, 3C–6C (1987).

Bolser et al., "Convergence of Phrenic and Cardiopulmonary Spinal Afferent Information on Cervical and Thoracic Spinothalamic Tract Neurons in the Monkey Implications for Referred Pain from the Diaphragm and Heart", *J. Neurophysiology*, vol. 65, No. 5, pp. 1042–1054 (1991).

Chandler et al., "A Mechanism of Cardiac Pain Suppression by Spinal Cord Stimulation: Implications for Patients With Angina Pectoris", *European Heart Journal*, V. 14, pp. 96–105 (1993).

Mannheimer et al., "Epidural spinal electrical stimulation in severe angina pectoris", *Br Heart J.*, V. 59, pp. 56–61 (1988).

Augustinsson, L.E., "Spinal Cord Electrical Stimulation in Severe Angina Pectoris: Surgical Technique Intraoperative Physiology, Complications and Side Effects", Pace, vol. 2, pp. 693–694 (1989).

González–Darder et al., "High Cervical Spinal Cord Stimulation for Unstable Angina Pectoris", *Stereotact Funct Neurosurg.*, 56: pp. 20–27 (1991).

Sanderson et al., "Epidural spinal electrical stimulation for severe angina: a study of its effects on symptoms, exercise tolerance and degree of ischaemia", *European Heart Journal*, V. 13, pp. 628–633 (1992).

(List continued on next page.)

*Primary Examiner*—William E. Kamm
*Assistant Examiner*—George R. Evanisko
*Attorney, Agent, or Firm*—Banner & Witcoff Ltd.

[57] ABSTRACT

Techniques for cardiac monitoring and angina pectoris treatment using a cardiac condition detector and stimulating electrode. The detector and electrode are implanted. Angina is relieved by transmitting electrical pulses to the stimulating electrode while the patient is giving an indication of an ischemic event that otherwise would be indicated by the angina.

23 Claims, 4 Drawing Sheets

OTHER PUBLICATIONS de Jongste et al., "Preliminary Results of a Randomized Study on the Clinical Efficacy of Spinal Cord Stimulation for Refractory Severe Angina Pectoris", *Acta Neurochir*, Supp. 58: pp. 161–164 (1993).

Anderson et al., "Does pain relief with spinal cord stimulation for angina conceal myocardial infarction", *Br. Heart J.*, 71: pp. 419–421 (1994).

de Jongste et al., "Efficacy of Spinal Cord Stimulation as Adjuvant Therapy for Intractable Angina Pectoris: A Prospective, Randomized Clinical Study", *JACC*, V. 23, No. 7, pp. 1592–1597 (1994).

de Jongste et al., "Stimulation Characteristics, Complications, and Efficacy of Spinal Cord Stimulation Systems in Patients with Refractory Angina: A Prospective Feasibility Study", *Pace*, vol. 17, pp. 1751–1760 (1994).

de Jongste et al., "Effects of Spinal Cord Stimulation on Mycardial Ischaemia During Daily Life in Patients with Severe Coronary Artery Disease", *Br. Heart J.*, 71: pp. 413–418 (1994).

Eliasson et al., "Therapy and Prevention, Safety aspects of spinal cord stimulation in severe angina pectoris", *Coronary Artery Disease*, 5: pp. 845–850 (1994).

Sanderson et al., "Spinal electrical stimulation for intractable angina—long–term clinical outcome and safety", *European Heart Journal*, vol. 15, pp. 810–814 (1994).

Anderson et al., "Spinal cord stimulation as a pain treatment for angina pectoris", *The Pain Clinic*, vol. 8, No. 4, pp. 333–339 (1995).

Hautvast et al., "Effect of Spinal Cord Stimulation on Myocardial Blood Flow Assessed by Positron Emission Tomography in Patients with Refractory Angina Pectoris", *Am. J. Cardiology*, vol. 77, pp. 462–467 (1996).

Eliasson et al., "Spinal cord stimulation in severe angina pectoris—presentation of current studies, indications and clinical experience", *Pain*, 65, pp. 169–179 (1996).

Murphy & Giles, "Intractable angina pectoris: management with dorsal column stimulation", *The Medical Journal of Australia*, vol. 14, p. 260 (1987).

METHOD AND APPARATUS FOR PROVIDING FEEDBACK TO SPINAL CORD STIMULATION FOR ANGINA

This application is a continuation of application Ser. No. 08/637,259, filed Apr. 25, 1996, now abandoned.

BACKGROUND OF THE INVENTION

1. Field of the Invention

This invention relates to techniques for relieving angina, and more particular relates to such techniques for detecting the occurrence of an ischemic event while angina is being relieved.

2. Description of the Related Art

Methods of detecting cardiac status using implanted (temporary or permanent) transducers exist and include detection of the S-T segment depression of an EKG waveform. There also have been proposals for using infrared energy as a means of recognizing an ischemia.

Spinal cord stimulation to treat intractable angina has been suggested. D. F. Murphy, et. al. describe the clinical results of such a technique in "Column Stimulation for Pain Relief from Intractable Angina Pectoris", Pain, Volume 28, 1987, at 363–368, incorporated herein by reference. Bourgeois (U.S. Pat. No. 5,058,584) describes a method and apparatus for applying the stimulation only when the subject is increasing physical activity and as such causes the occurrence of angina. Bourgeois assumes blood flow to the heart is increased by spinal cord stimulation. Therefore the application of stimulation during times of increased activity will increase coronary blood flow and reduce the likelihood that the patient will experience pain. However, there is still controversy about whether the stimulation of the spinal cord increases the blood flow to the heart thereby reducing angina or if it merely masks the pain. Of concern is the possibility that by masking angina pain using spinal cord stimulation, the patient may be put at greater risk for an infarct by causing the patient to ignore or not perceive the signs of cardiac ischemia and overexert himself This invention addresses that problem.

SUMMARY OF THE INVENTION

The invention can be used for cardiac monitoring and angina pectoris treatment of a patient by using a cardiac condition detector and a stimulating electrode. According to a preferred embodiment, the detector is placed at a recording site either adjacent the patient or in the patient. A stimulating electrode is implanted adjacent the spinal cord or in the spinal cord of the patient. Indicia of the condition of the heart muscle of the patient are received at the detector and are processed to detect the occurrence of an ischemic event. An indication of the occurrence of the ischemic event detectable by the patient is produced. Electrical pulses suitable for stimulating the spinal cord to reduce angina are also generated. The pulses are gated to the stimulating electrode so that the angina pectoris is reduced while the patient is given an indication of an ischemic event that otherwise would be indicated by the angina pectoris.

By using the foregoing techniques, angina pectoris can be relieved while the patient is simultaneously protected against undo exertion following an ischemic event.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
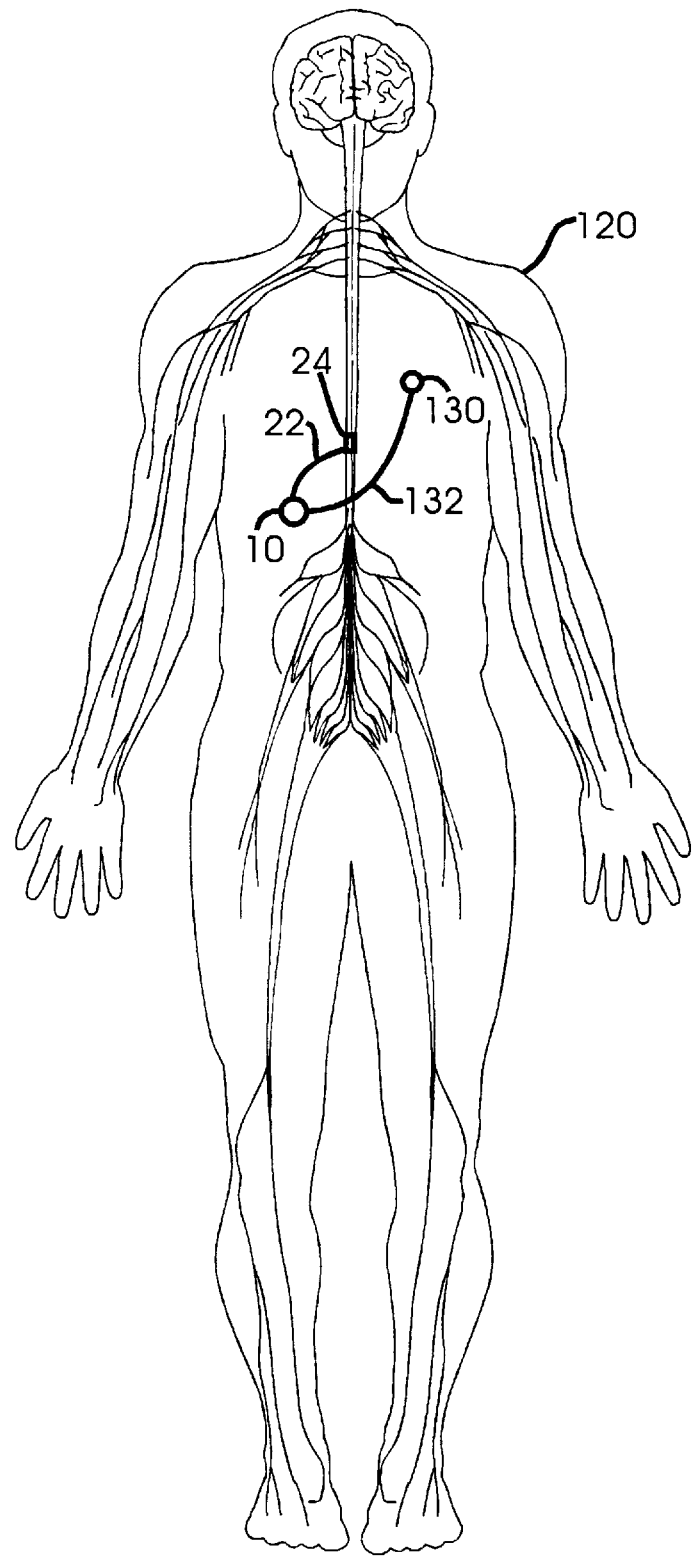
FIG. 1 is a diagrammatic view of a patient in which a preferred form of the invention has been implanted.
Figure 2:
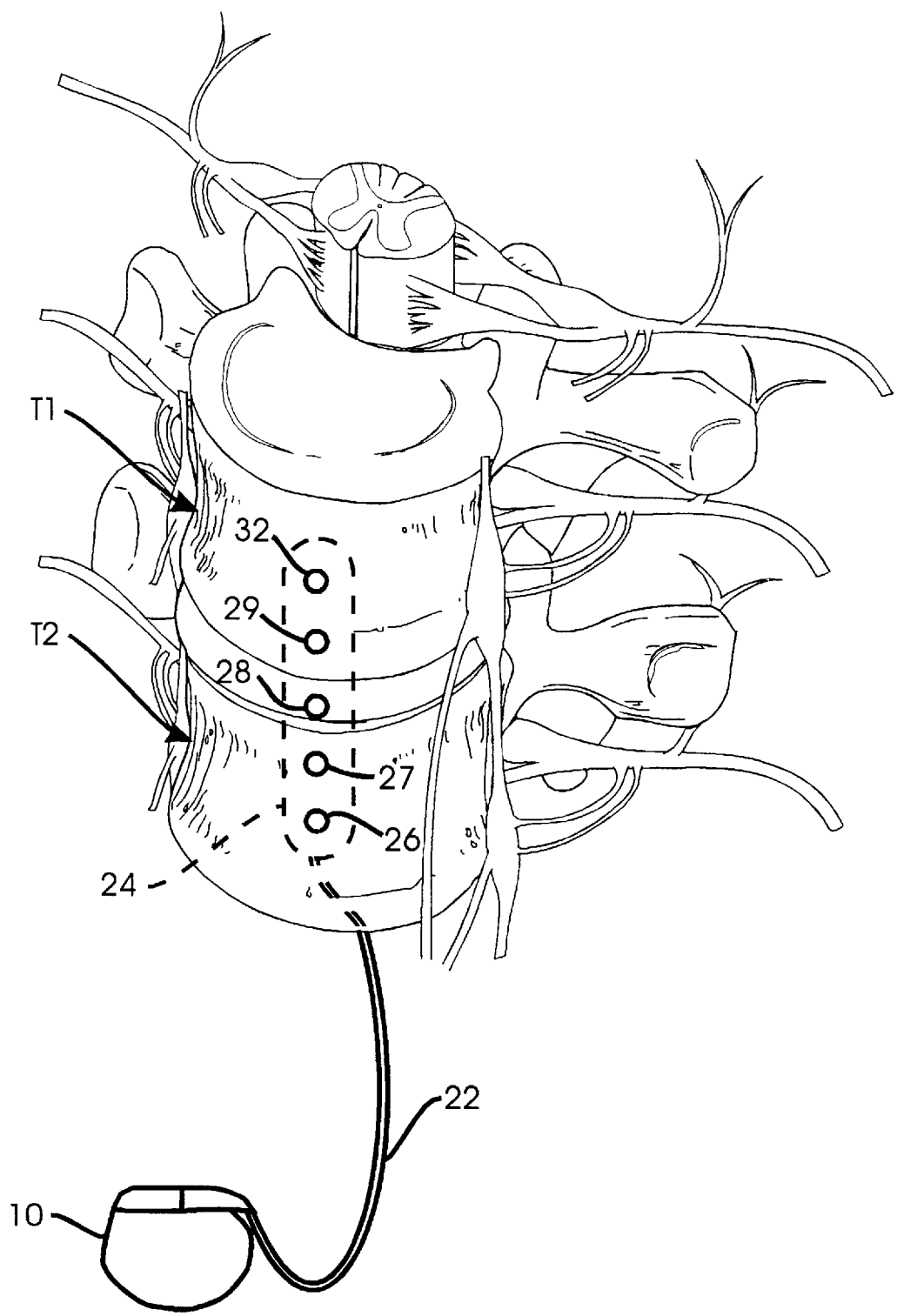
FIG. 2 is a diagrammatic view of a portion of the vertebral column of the patient shown in FIG. 1 in which a preferred embodiment of the invention has been implanted.
Figure 3:
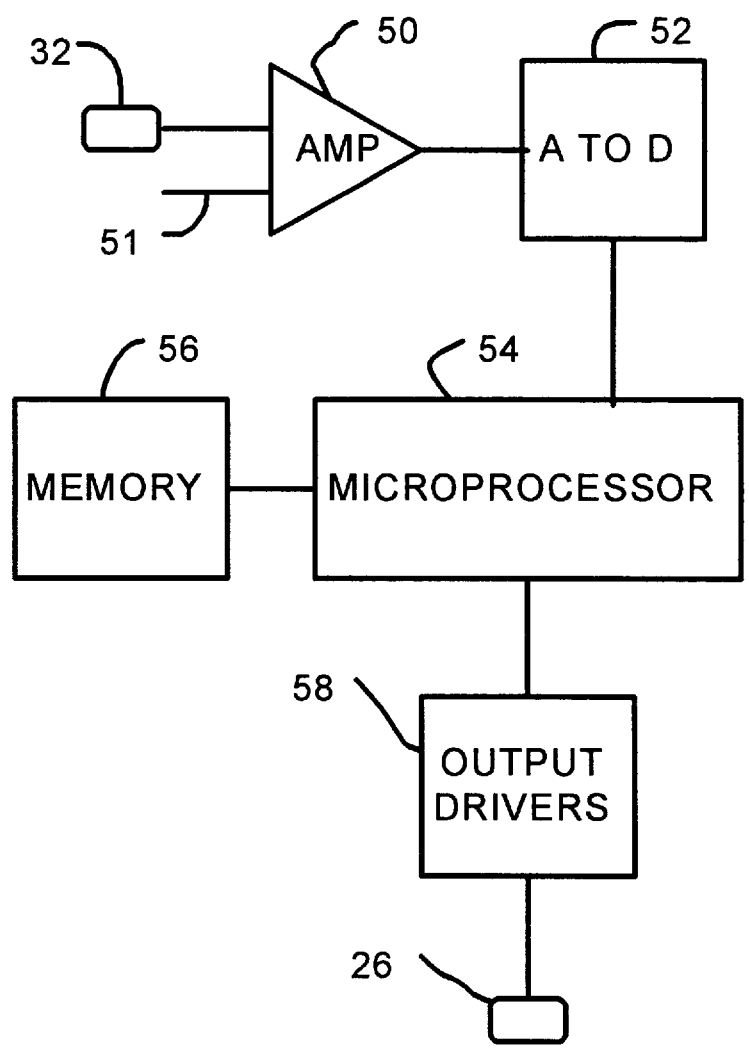
FIG. 3 is a block diagram of electrical circuitry implanted in the patient.

Referring to FIGS. 1 and 2, a preferred form of the invention comprises an implantable pulse generator 10 manufactured by Medtronic, Inc. under the trademark Itrel II. Device 10 preferably is implanted in the abdomen under the rib cage of a patient 120 and is connected by an extension cable 22 to a conventional lead in the form of a paddle 24 that is implanted near or in the spinal column of patient 120. Cable 22 is inserted into the spinal column and threaded part way up the spinal column to a position over the dorsal aspect of the spinal cord segment in the thoracic area of vertebrae T-1 to T-2. Positioned on paddle 24 are stimulating electrodes 26–29, as well as a cardiac condition detector in the form of a recording electrode 32. Placement of both stimulating and recording electrodes on a single paddle is an important feature which eliminates the necessity of additional hardware being implanted in the patient. Referring to FIG. 3, device 10 includes an amplifier 50 having an output connected to an analog to digital converter 52 in the manner shown. One input of amplifier 50 is connected to recording electrode 32. Other inputs of the amplifier may be connected through a conductor 51 to any other physical signals within patient 120 indicative of ischemia of the cardiac muscle.

Detector 32 receives an indicia of the condition of the heart muscle of patient 120. The indicia may comprise electrical potentials caused by the excitation of the heart muscle of the patient. These electrical potentials are the same potentials normally resulting in an electrocardiogram. The potentials are amplified by amplifier 50 and converted to digital form by converter 52. The digital form of the electrical potentials is stored by a microprocessor 54 and a memory 56. Under control of an algorithm stored in memory 56, the microprocessor can produce signals to output drivers 58 that provide stimulation electrical pulses to any of stimulating electrodes 26–29 (FIG. 2).

Figure 4:
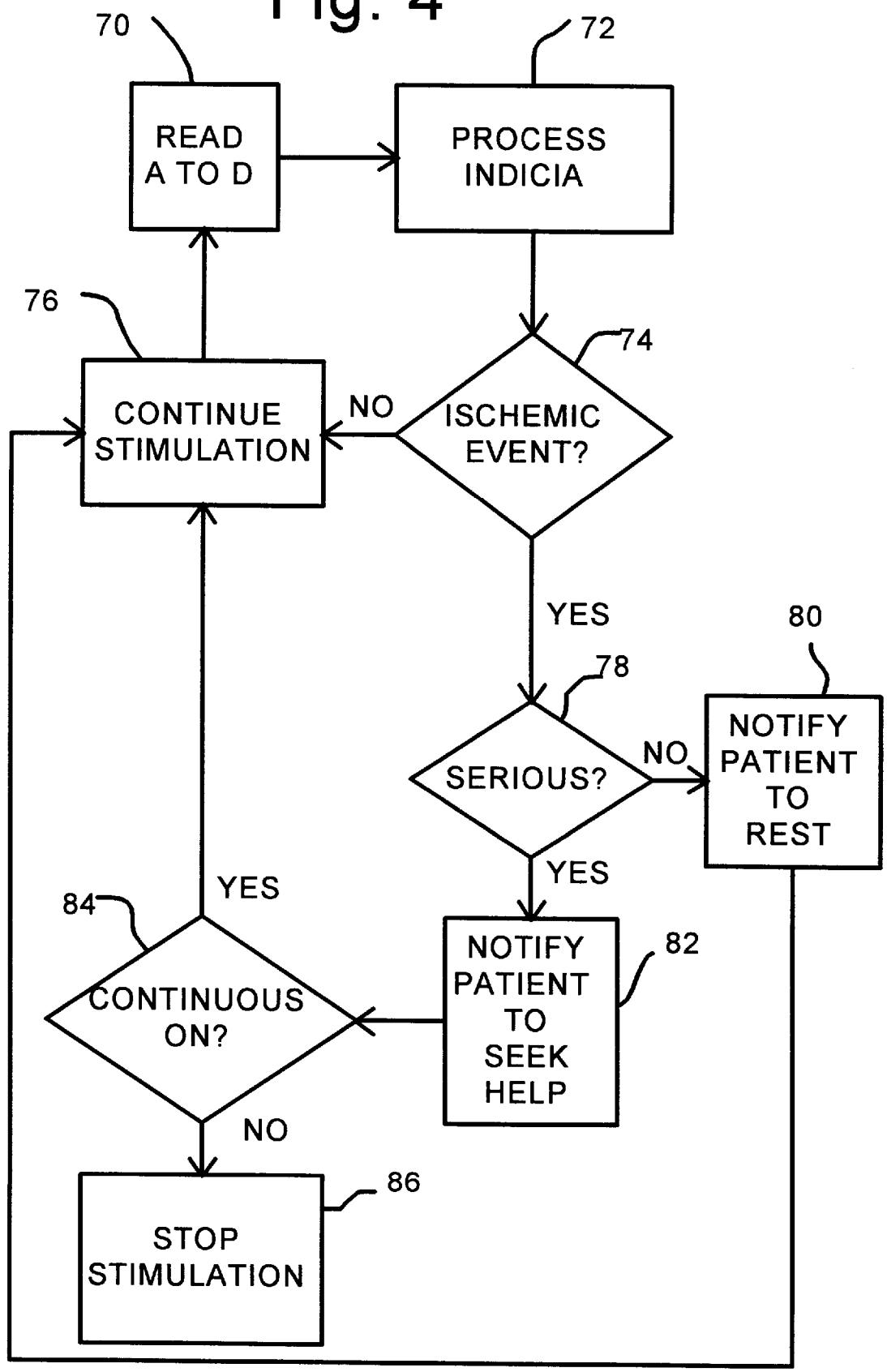
FIG. 4 is a flow diagram illustrating an algorithm executed by the electrical circuitry in order to relieve angina and simultaneously indicate the occurrence of an ischemic event to the patient.

Referring to FIG. 4, in step 70, microprocessor 54 reads analog to digital converter 52. In step 72, the indicia converted to digital form are processed. The processing may include any of the well-known methods of detecting cardiac status, such as analyzing the wave form of the electrical potentials caused by the excitation of the heart muscle of patient 120. In particular, the processing may analyze the S-T segment of the wave form of the potentials for a depression indicating an ischemic event. Publications describing such processing include the following: Hammermeister, K. E., DeRouen, T. A., and Dodge, H. T.; Variables predictive of survival in patients with coronary disease. Selection by univariate and multivariate analyses from the clinical, electrocardiographic, exercise, arteriographic and quantitative angiographic evaluation.

Circulation, 59:421, 1979 and Cohn, P. F., Total Ischemic Burden: Pathophysiology and Prognosis. American journal of Cardiology, No. 59, 3C–6C, 1987.

Based on the processing done in step 72, in step 74, the microprocessor determines whether an ischemic event has occurred. If no such event has occurred, stimulation is continued by providing stimulation pulses to any of electrodes 26–29 through output drivers 58 (FIG. 3). If an ischemic event has occurred, in step 78, the algorithm determines whether it is serious or not. If it is not serious, in step 80, the patient is notified to rest. If the event is serious, in step 82, the patient is notified to seek help in general, and medical help in particular. The algorithm continues in step 84 by determining whether device 10 has been set for continuous stimulation in order to relieve angina. If device 10 has been set for continuous stimulation, the stimulation is continued through step 76. If the device has not been set for continuous stimulation, then the stimulation is stopped in step 86 as long as the algorithm indicates that a serious ischemic event is occurring.

Still referring to FIG. 4, steps 80 and 82 can be implemented either by providing an audible signal to the patient or by varying the type of stimulation applied to stimulating electrodes 26–29 in a manner which can be detected by the patient. For example, the audible signal could be implemented by a beeper carried in the pocket of the patient capable of receiving a telemetered signal from the implanted device. Alternatively, the sound could come from a generator that is a part of the implanted pulse generator (IPG), the sound being able to travel outside of the body to be heard by the patient. Instead of sound, sensory stimulation could be accomplished by electrically stimulating the tissue around the subcutaneous pocket that the pulse generator is implanted in through an electrode that is made to be part of the IPG package or by stimulating the spinal cord. Varying the stimulation to the spinal cord could be implemented by varying the stimulus pattern of pulses in a way that the patient can recognize.

Referring to FIG. 1, the cardiac condition detector also may take the form of a recording electrode 130 positioned in the chest cavity of the patient that is connected to device 10 by a cable 132. Additional recording electrodes can be placed in various parts of the patient's body in order to simulate the electrodes typically used for an EKG. Each of the recording electrodes may be connected to device 10 through implanted cables.

Alternatively, the cardiac condition detector may take the form of an infrared device placed adjacent to the patient's heart. This type of cardiac condition detector is described in U.S. Pat. No. 5,067,960 filed by Grandjean incorporated herein by reference. Alternatively, the cardiac condition detector could take the form of a sensor monitoring coronary sinus blood pH and/or oxygen saturation as described by Obel and Bourgeois in U.S. Pat. No. 5,199,428 incorporated herein by reference.

By using the foregoing techniques, angina may be relieved by the application of pulses from device 10 to stimulating electrodes 26–29. While the angina is being relieved, the patient may be informed of the occurrence of an ischemic event without the need to stop the stimulation that relieves angina. This technique minimizes the risk that the patient may overexert himself due to a failure to perceive the angina which is being relieved by the application of pulses to the stimulating electrodes.

Those skilled in the art recognize that the preferred embodiments may be altered and modified without departing from the true spirit and scope of the invention as defined in the appended claims.

I claim:

1. A method of cardiac monitoring and angina pectoris treatment of a patient by using a cardiac condition detector and a stimulating electrode, comprising the steps of:

placing said cardiac condition detector at a recording site adjacent said patient or in said patient;

implanting said stimulating electrode adjacent a spinal cord or in said spinal cord of said patient;

receiving an indicia of the condition of a heart muscle of said patient through said detector;

processing said indicia to detect an occurrence of an ischemic event;

generating an indication detectable by said patient of said occurrence of said ischemic event in response to said processing;

generating electrical pulses suitable for stimulating said spinal cord to reduce angina; and gating said pulses to said stimulating electrode, whereby said angina pectoris is reduced while the patient is given an indication of an ischemic event that otherwise would be indicated by said angina pectoris.

2. A method, as claimed in claim 1, wherein said recording site is adjacent said spinal cord or in said spinal cord of said patient.

3. A method, as claimed in claim 1, wherein said recording site is in a chest cavity.

4. A method, as claimed in claim 1, wherein said indicia comprises electrical potentials caused by an excitation of said heart muscle of said patient.

5. A method, as claimed in claim 4, wherein said step of processing comprises the step of analyzing a waveform of said electrical potentials.

6. A method, as claimed in claim 5, wherein said step of analyzing said waveform comprises the step of a the S-T segment of said waveform for a depression.

7. A method, as claimed in claim 5, wherein said steps of placing and implanting comprise the step of placing said detector and said stimulating electrode on a lead.

8. A method, as claimed in claim 7, wherein said method uses a signal generator and wherein said method further comprises the step of implanting said signal generator in said patient.

9. A method, as claimed in claim 1, wherein said indicia comprises infrared radiation.

10. A method, as claimed in claim 9, wherein said step of processing comprises the step of analyzing said infrared radiation.

11. A method, as claimed in claim 1, wherein said step of generating an indication comprises the step of varying the pulses applied to said stimulating electrode so that said patient can sense a change in the stimulation applied to said electrode by said pulses.

12. A method, as claimed in claim 1, wherein said step of generating an indication comprises the step of generating a sound.

13. Apparatus for cardiac monitoring and angina pectoris treatment of a patient comprising:

a cardiac condition detector adapted to be placed at a recording site adjacent said patient or in said patient for generating an indicia of the condition of a heart muscle of said patient;

a stimulating electrode adapted to be implanted adjacent a spinal cord or in said spinal cord of said patient;

means for processing said indicia to detect an occurrence of an ischemic event;

means for generating an indication detectable by said patient of an occurrence of said ischemic event in response to said processing;

means for generating electrical pulses suitable for stimulating said spinal cord to reduce angina; and means for gating said pulses to said stimulating electrode, whereby said angina pectoris is reduced while the patient is given an indication of an ischemic event that otherwise would be indicated by said angina pectoris.

14. Apparatus, as claimed in claim 13, wherein said recording site is adjacent said spinal cord or in said spinal cord of said patient.

15. Apparatus, as claimed in claim 13, wherein said recording site is in a chest cavity of said patient.

16. Apparatus, as claimed in claim 13, wherein said indicia comprises electrical potentials caused by an excitation of said heart muscle of said patient.

17. Apparatus, as claimed in claim 16, wherein said means for processing comprises means for analyzing a waveform of said electrical potentials.

18. Apparatus, as claimed in claim 17, wherein said means for analyzing said waveform comprises means for analyzing a S-T segment of said waveform for a depression.

19. Apparatus, as claimed in claim 13, wherein said detector and said stimulating electrode are located on a lead.

20. Apparatus, as claimed in claim 13, wherein said indicia comprises infrared radiation.

21. Apparatus, as claimed in claim 20, wherein said means for processing comprises means for analyzing said infrared radiation.

22. Apparatus, as claimed in claim 13, wherein said means for generating an indication comprises means for varying the pulses applied to said stimulating electrode so that said patient can sense a change in the stimulation applied to said electrode by said pulses.

23. Apparatus, as claimed in claim 13, wherein said means for generating an indication comprises means for generating a sound.

* * * * *